United States Patent
Shin et al.

(10) Patent No.: US 12,061,358 B2
(45) Date of Patent: Aug. 13, 2024

(54) METHOD FOR MANUFACTURING OPTICAL FIBER EMITTING PLASMA LIGHT

(71) Applicant: REV-MED, INC., Seongnam-si (KR)

(72) Inventors: Bong Geun Shin, Suwon-si (KR); Yong Man Cho, Seoul (KR)

(73) Assignee: Rev-Med, Inc., Seongnam-si (KR)

( * ) Notice: Subject to any disclaimer, the term of this patent is extended or adjusted under 35 U.S.C. 154(b) by 559 days.

(21) Appl. No.: 17/413,685

(22) PCT Filed: Nov. 19, 2019

(86) PCT No.: PCT/KR2019/015884
§ 371 (c)(1),
(2) Date: Jun. 14, 2021

(87) PCT Pub. No.: WO2021/095955
PCT Pub. Date: May 20, 2021

(65) Prior Publication Data
US 2022/0011513 A1     Jan. 13, 2022

(30) Foreign Application Priority Data

Nov. 11, 2019   (KR) .................. 10-2019-0143167

(51) Int. Cl.
*G02B 6/287*    (2006.01)
*C03B 37/15*    (2006.01)
(Continued)

(52) U.S. Cl.
CPC ............. *G02B 6/25* (2013.01); *G02B 6/4296* (2013.01)

(58) Field of Classification Search
CPC ............ C03B 37/14–15; G02B 6/4296; G02B 6/241; G02B 6/25; G16H 20/30–40
See application file for complete search history.

(56) References Cited

U.S. PATENT DOCUMENTS 5,029,528 A    7/1991   Paisley
9,784,912 B2   10/2017  Kim et al.

FOREIGN PATENT DOCUMENTS

JP       2006-14776 A     1/2006
KR  10-2006-0108469 A    10/2006
(Continued)

OTHER PUBLICATIONS

KR 10-2006-0108469 A (Kang) Oct. 18, 2006 (English language machine translation). [online] [retrieved Dec. 18, 2023]. Retrieved from: Clarivate Analytics. (Year: 2006).*

(Continued)

*Primary Examiner* — Erin Snelting
(74) *Attorney, Agent, or Firm* — Knobbe, Martens, Olson & Bear, LLP

(57) ABSTRACT

A method for manufacturing an optical fiber emitting plasma light includes a coating removal step of removing a coating of an optical fiber; a photocatalyst application step of applying a photocatalyst to an end surface of a core layer of the optical fiber from which the coating has been removed through the coating removal step; and a molding step of molding the end surface of the core layer into a curved surface by applying a laser to the core layer of the optical fiber applied with the photocatalyst through the photocatalyst application step. The method for manufacturing an optical fiber including the above processes may be effectively used for therapy such as plasma disc coagulation therapy (PDCT) by converting the applied laser light into plasma light.

7 Claims, 4 Drawing Sheets

Example 1

Comparative Example 1

(51) Int. Cl.
*G02B 6/25* (2006.01)
*G02B 6/42* (2006.01)

(56) References Cited

FOREIGN PATENT DOCUMENTS

| KR | 10-2008-0079006 A | 8/2008 |
| KR | 10-2019-0048126 A | 5/2019 |

OTHER PUBLICATIONS

Office Action of Korean Patent Application No. 10-2019-0143167—4 pages (Apr. 19, 2021).
International Search Report of PCT Application No. PCT/KR2019/015884—4 pages (Aug. 10, 2020).

* cited by examiner

Example 1          Comparative Example 1

METHOD FOR MANUFACTURING OPTICAL FIBER EMITTING PLASMA LIGHT

CROSS-REFERENCE TO RELATED APPLICATION

This application claims priority to and the benefit of Korean Patent Application No. 10-2019-0143167, filed on Nov. 11, 2019, the disclosure of which is incorporated herein by reference in its entirety.

TECHNICAL FIELD

The present invention relates to a method for manufacturing an optical fiber emitting plasma light, and more specifically, the present invention relates to a method for manufacturing an optical fiber emitting plasma light, which can be effectively used for therapy such as plasma disc coagulation therapy (PDCT) by converting the applied laser light into plasma light.

BACKGROUND ART

Recently, low back pain therapy (PLDD) that does not cause a burden on the body is attracting attention as a low-invasive treatment, and PLDD is an abbreviation of percutaneous laser disk decompression, which is a treatment method that makes a hole in the skin with an injection needle, inserts the tip of a thin laser fiber into the side of the intervertebral cartilage, and irradiates a laser to cauterize the contents of the intervertebral cartilage and to create a space to restore the protruding hernia to its original shape.

As a laser treatment for intervertebral hernia, PLDD began in 1986 at the Medical University of Graz in Austria and has since been widely distributed in European countries and the United States. In Japan, it has been practiced mainly in private facilities since 1990s, but due to its lack of effect, it has not received much attention at academic conferences and the like.

PLDD is performed by a process of piercing with a needle having a diameter of about 1.2 mm under local anesthesia, introducing a 0.4 mm laser optical fiber therein, and irradiating laser light into the intervertebral disc by light guiding, and as the area irradiated with laser light generates high heat and evaporates, the surroundings are solidified. Through the above process, the pressure of the intervertebral disc is lowered, the hernia is returned, and nerve pressure is resolved. The irradiation time of laser is about 3 to 5 minutes, the entire operation takes 10 to 15 minutes, and the recovery is fast enough to be able to return home after 2 to 3 hours following the operation.

However, the aforementioned PLDD uses laser light, and a diffusing phenomenon occurs for normal light as it is further away from a light source. On the other hand, laser light is a straight light that does not diffuse well, and since it affects not only the target treatment area, but also it passes through the target to affect the area other than the target, side effects may occur depending on the application site.

In addition, the energy transmission device for general laser light uses an ARM, which is an optical transmission device in a joint structure with a reflector, and since a laser fiber for general medical use has strong linearity, which is a characteristic of laser light, and outputs laser light having a single wavelength, it has high energy density and can damage the internal organs of the human body due to its linearity. Thus, there have been problems where it is not suitable for a procedure performed by inserting it inside the human body.

DISCLOSURE

Technical Problem

An object of the present invention is to provide a method for manufacturing an optical fiber emitting plasma light, which can be effectively used for therapy such as plasma disc coagulation therapy (PDCT) by converting the applied laser light into plasma light.

Technical Solution

The object of the present invention is achieved by providing a method for manufacturing an optical fiber emitting plasma light, including a coating removal step of removing a coating of an optical fiber; a photocatalyst application step of applying a photocatalyst to an end surface of a core layer of the optical fiber from which the coating has been removed through the coating removal step; and a molding step of molding the end surface of the core layer into a curved surface by applying a laser to the core layer of the optical fiber applied with the photocatalyst through the photocatalyst application step.

According to a preferred feature of the present invention, the core layer of the optical fiber is made of silica.

According to a more preferred feature of the present invention, the photocatalyst application step is performed by immersing the end surface of the core layer of the optical fiber in the photocatalyst to a depth of 0.4 to 0.6 mm while applying a laser to the core layer of the optical fiber.

According to a much more preferred feature of the present invention, the photocatalyst is made of 100 parts by weight of titanium oxide, 400 to 500 parts by weight of manganese dioxide, 350 to 450 parts by weight of epoxy, and 45 to 55 parts by weight of carbon.

According to a still more preferred feature of the present invention, the molding step is performed by applying a laser while the optical fiber is erected such that the end surface of the core layer of the optical fiber applied with the photocatalyst through the photocatalyst application step is positioned on an upper surface.

According to a still more preferred feature of the present invention, the laser is applied under a condition of 8 to 10 W, a pulse width of 50 ms, and an off time of 50 ms.

According to a still more preferred feature of the present invention, the laser is irradiated for 1.5 to 2.5 seconds.

Advantageous Effects

The method for manufacturing an optical fiber emitting plasma light according to the present invention exhibits an excellent effect of providing an optical fiber emitting plasma light, which can be effectively used for therapy such as plasma disc coagulation therapy (PDCT) by converting the applied laser light into plasma light.

BEST MODE

Figure 1:
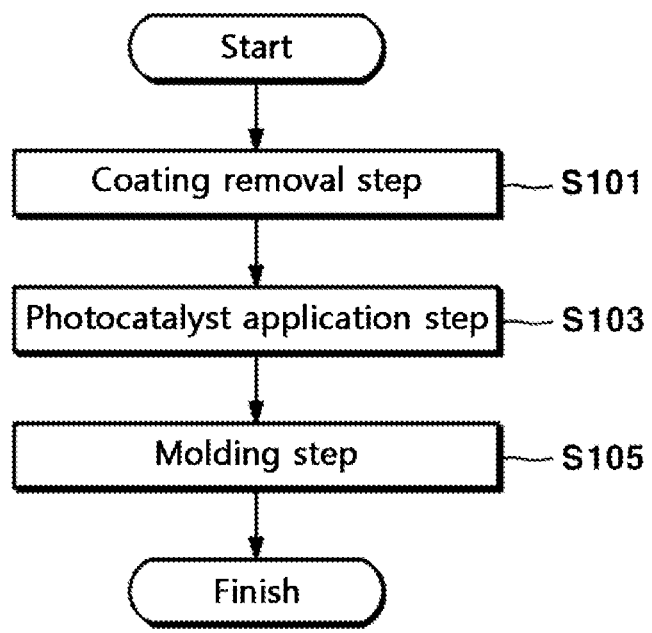
FIG. 1 is a flow chart illustrating the method for manufacturing an optical fiber emitting plasma light according to the present invention.

Hereinafter, while preferred exemplary embodiments of the present invention and the physical properties of each component will be described in detail, this is for describing in detail enough that one of ordinary skill in the art can easily carry out the invention, and this does not mean that the technical spirit and scope of the present invention are limited thereby.

The method for manufacturing an optical fiber emitting plasma light according to the present invention includes a coating removal step S101 of removing a coating of an optical fiber, a photocatalyst application step S103 of applying a photocatalyst to an end surface of a core layer of the optical fiber from which the coating has been removed through the coating removal step S101, and a molding step S105 of molding the end surface of the core layer into a curved surface by applying a laser to the core layer of the optical fiber applied with the photocatalyst through the photocatalyst application step S103.

The coating removal step S101 is a step of removing the coating of an optical fiber and includes a process of removing a coating formed on an optical fiber using a stripping tool or the like.

The coating of the optical fiber is conventionally made of an outer cover of a Teflon material, is interposed between the outer cover and the core layer, and includes an inner cover made of a hard polymer.

In addition, laser light is transmitted through the core layer, and in this case, it is preferable that the core layer is made of a silica material.

The photocatalyst application step S103 is a step of applying a photocatalyst to the end surface of the core layer of the optical fiber from which the coating has been removed through the coating removal step S101, and it is performed by immersing the end surface of the core layer of the optical fiber in the photocatalyst to a depth of 0.4 to 0.6 mm while applying a laser to the core layer of the optical fiber from which the coating has been removed.

More specifically, while a laser having a wavelength of 800 to 1,064 nm, more preferably, 980 nm is applied to the core layer of the optical fiber from which the coating has been removed through the coating removal step S101 at 5 to 8 W and a pulse width of 50 ms, the end surface of the core layer of the optical fiber is immersed in the photocatalyst such that the photocatalyst component is applied to the end surface of the optical fiber.

If a laser is not applied to the core layer of the optical fiber, the photocatalyst component may not be applied to the end surface of the optical fiber, and the reason is that when the laser is applied to the core layer of the optical fiber, the temperature of the core layer of the optical fiber rises such that while melting in a small amount, the photocatalyst component is applied to the end surface of the core layer of the optical fiber.

In addition, if the end surface of the core layer of the optical fiber core is immersed in the photocatalyst to a depth of less than 0.4 millimeters, the photocatalyst component is not sufficiently applied, and it may be difficult to mold the end surface of the core layer of the optical fiber into a curved line during the molding process performed in the molding step S105 as the photocatalyst component is excessively applied to the end surface of the core layer of the optical fiber.

In this case, the photocatalyst is made of 100 parts by weight of titanium oxide, 400 to 500 parts by weight of manganese dioxide, 350 to 450 parts by weight of epoxy, and 45 to 55 parts by weight of carbon, and while it is preferable to be made of 100 parts by weight of titanium oxide, 450 parts by weight of manganese dioxide, 400 parts by weight of epoxy, and 50 parts by weight of carbon, the titanium oxide, manganese dioxide, and carbon components excluding the epoxy are used by mixing with the epoxy component after powdering.

The molding step S105 is a step of molding the end surface of the core layer into a curved surface by applying a laser to the core layer of the optical fiber applied with the photocatalyst through the photocatalyst application step 103, and it is performed by applying a laser while the optical fiber is erected such that the end surface of the core layer of the optical fiber applied with the photocatalyst through the photocatalyst application step S103 is positioned on an upper surface. When a laser is applied to the erected optical fiber, the end surface of the core layer of the optical fiber is in a state where the photocatalyst component with very high light absorption is applied, and high heat is instantaneously generated on the end surface of the core layer of the optical fiber as the laser light is transmitted or reacts with little loss, and the end surface of the core layer of the optical fiber melts to form a curved surface.

Through the above process, the curved portion formed on the end surface of the core layer of the optical fiber is in a transparent and clean state, and when laser light is applied to the optical fiber in which the end surface is formed to be a curved surface as the above, it is converted into plasma light.

If the curved surface is formed by simply heating the end surface of the core layer of the optical fiber without undergoing the above process, debris due to heating is generated or the curved portion is carbonized or transformed, resulting in a decrease in light transmittance.

In addition, if the end surface of the core layer of the optical fiber is processed into the shape of a curved surface through physical processing, the light transmittance may be significantly reduced due to fine scratches and the like on the surface, and the laser light may not be converted to plasma light.

In this case, the laser is applied under a condition of 8 to 10 W, a pulse width of 50 ms, and an off time of 50 ms, and it is preferably irradiated for 1.5 to 2.5 seconds. If the irradiation time of the laser is less than 1.5 seconds, the end surface of the core layer of the optical fiber may not be formed into a curved surface, and when the irradiation time of the laser is more than 2.5 seconds, the end surface of the core layer of the optical fiber is excessively melted, and due to a flowing phenomenon, it is difficult to form a curved surface, and a carbonization phenomenon occurs.

Modes of the Invention

Hereinafter, the method for manufacturing an optical fiber emitting plasma light according to the present invention and the physical properties of the optical fiber manufactured through the manufacturing method will be described by way of examples.

Preparation Example 1

100 parts by weight of titanium oxide, 450 parts by weight of manganese dioxide, and 50 parts by weight of carbon were mixed and pulverized to prepare a pulverized product, and then, a photocatalyst was prepared by mixing and stirring 400 parts by weight of epoxy based on 100 parts by weight of titanium oxide contained in the pulverized product.

Example 1

After removing the coating of an optical fiber to prepare a core layer (silica) of the optical fiber, while the end surface of the core layer of the optical fiber was immersed in the photocatalyst prepared through Preparation Example 1 above to a depth of 0.5 mm, a 980 nm diode laser (output of 6.5 W and a pulse width of 50 ms) was applied by one shot to the photocatalyst to apply the photocatalyst on the end surface of the optical fiber. While the optical fiber was erected such that the end surface of the optical fiber applied with the photocatalyst was positioned on an upper surface, a 980 nm diode laser (an output of 9 W, a pulse width of 50 ms, and an off time of 50 ms) was applied to the optical fiber for 2 seconds to manufacture an optical fiber emitting plasma light through a process of melting the end of the optical fiber to mold into a curved line.

Comparative Example 1

The core layer (silica) of an optical fiber from which the coating has been removed.

Comparative Example 2

The core layer (silica) of an optical fiber core manufactured by physically processing the end surface of the core layer of the optical fiber, from which the coating has been removed, into a columnal shape.

The core layers of the optical fibers manufactured through Example 1 and Comparative Example 1 above were photographed and shown in FIG. 2 below.

Figure 2:
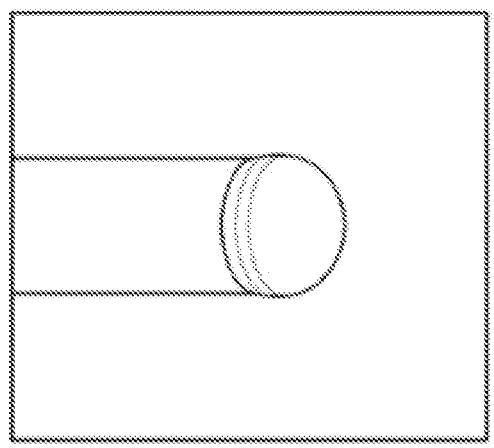
FIG. 2 is a diagram illustrating the end surfaces of core layers of optical fibers manufactured through Example 1 and Comparative Example 1 of the present invention.
Figure 2:
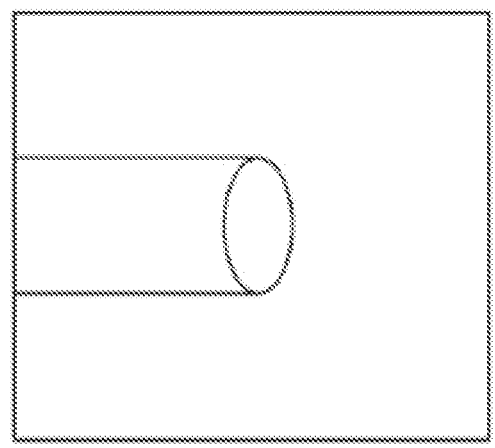

As shown in FIG. 2 below, it can be seen that the end surface of the optical fiber manufactured through Example 1 of the present invention was formed in a curved line.

In addition, the wavelengths were measured with an optical wavelength measurement device and shown in FIG. 3 below, after applying a 980 nm wavelength laser to an optical fiber manufactured through Example 1 (indicated in purple), applying a 980 nm wavelength laser to an optical fiber manufactured through Comparative Example 1 (indicated in green), and applying a 1,064 nm wavelength Nd-Yag to an optical fiber manufactured through Comparative Example 2 (indicated in red).

Figure 3:
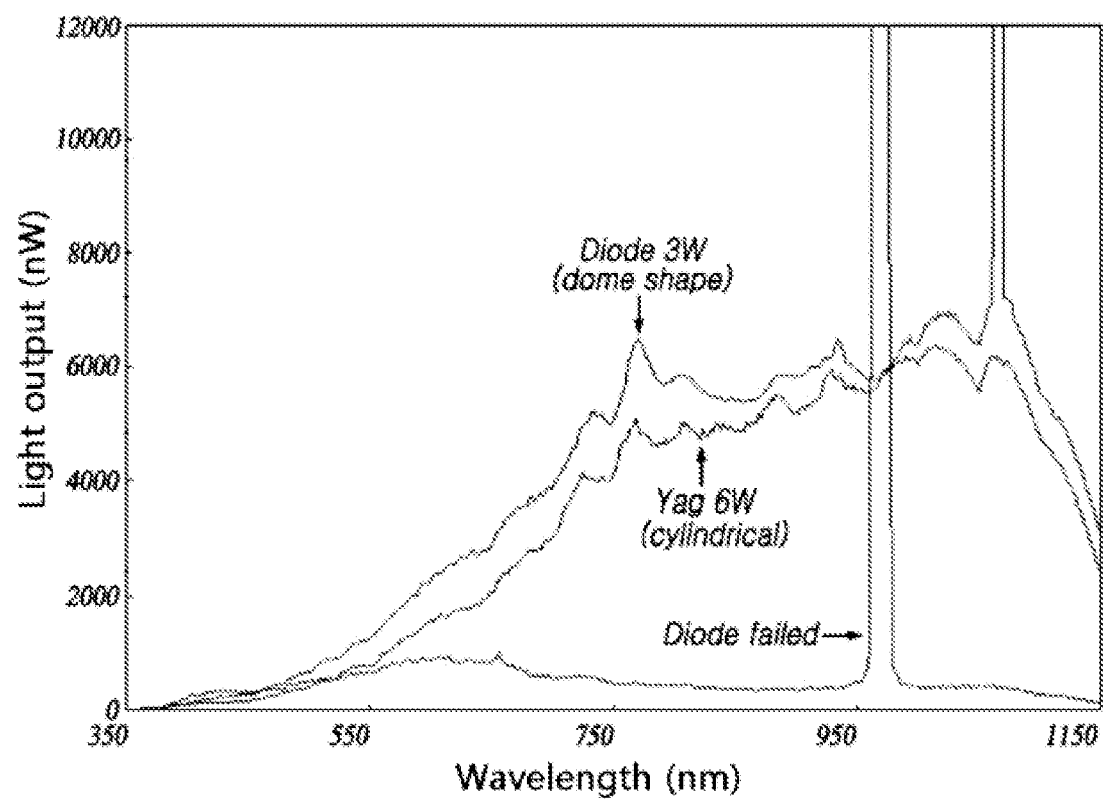
FIG. 3 is a graph showing the wavelengths measured with an optical wavelength measurement device, after applying a 980 nm wavelength laser to an optical fiber manufactured through Example 1 of the present invention (indicated in purple), applying a 980 nm wavelength laser to an optical fiber manufactured through Comparative Example 1 (indicated in green), and applying a 1,064 nm wavelength Nd-Yag to an optical fiber manufactured through Comparative Example 2 (indicated in red).

As shown in FIG. 3 below, the green line is the unprocessed optical fiber of Comparative Example 1, and it can be seen that the original laser characteristics remained strong. The purple line is a result of using the optical fiber whose end surface was processed through Example 1 to experiment with plasma light at a laser output of 3 W, and it was determined that it was a broadband ray with a flat peak of about 750 to 1,100 nm (the original 980 nm laser ray was not detected, and it means that one wavelength was changed to multiple wavelengths at the end of the fiber, which proves that the laser light was converted to plasma light).

In addition, the red line was irradiated with Nd-Yag, and it was tested at a laser output of 6 W with the core layer of the optical fiber manufactured in a columnar shape through Comparative Example 2. Certainly, plasma light was emitted, and it can be seen that the original Nd:YAG laser light also existed strongly.

In addition, in the above test, it was confirmed that the center temperature of plasma light reached 3,000° C., and since the actual PDCT procedure was performed at about 25 W, the center temperature of plasma was quite high, but it was confirmed that the temperature of the part except the central portion was stable at around 35° C. at 3 mm away from the center.

In addition, after applying a 980 nm wavelength laser to the optical fiber emitting plasma light manufactured in Example 1 above, the end surface of the core layer of the optical fiber was photographed and shown in FIG. 4 below.

Figure 4:
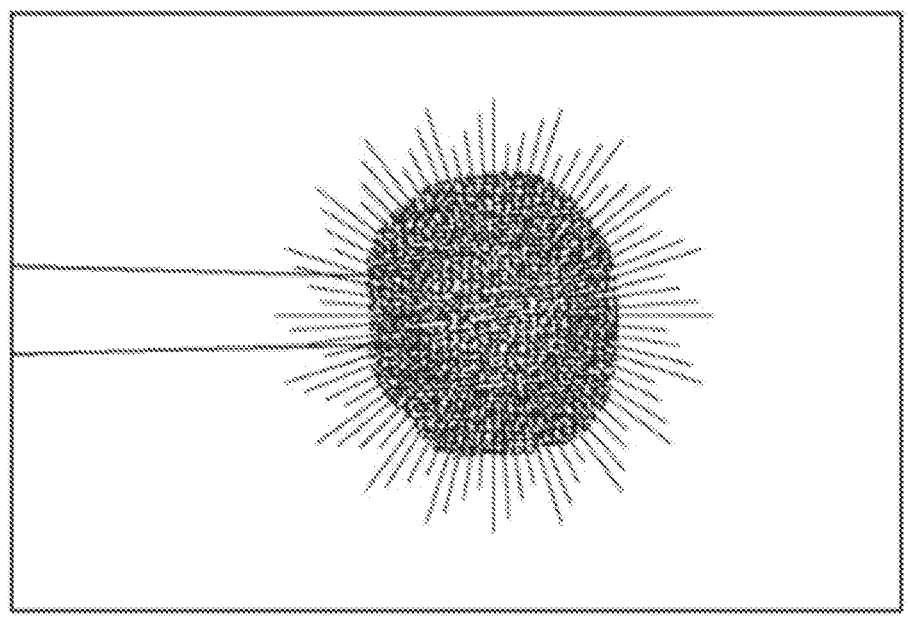
FIG. 4 illustrates an image of the end surface of a core layer of an optical fiber after applying a 980 nm wavelength laser to an optical fiber emitting plasma light, which was manufactured through Example 1 of the present invention.

As shown in FIG. 4 below, it can be seen that plasma light was diffused while drawing a concentric circle in the optical fiber manufactured through Example 1 of the present invention, and the diffusion of plasma light proceeded during the procedure within the narrow intervertebral disc such that the convenience of the procedure may be promoted. Since the core layer of the optical fiber whose end surface is molded into a curved line reduces the possibility of damaging the intervertebral disc tissue or damaging the core layer of the optical fiber during the procedure, it shows an effect of greatly reducing the possibility that the optical fiber remains in the body tissues after the procedure.

Therefore, the method for manufacturing an optical fiber emitting plasma light according to the present invention provides an optical fiber emitting plasma light, which can be effectively used for therapy such as plasma disc coagulation therapy (PDCT) by converting the applied laser light into plasma light.

In the above, although specific exemplary embodiments of the present invention have been described and illustrated, the present invention is not limited to the described exemplary embodiments, and it is apparent to one of ordinary skill in the art that various modifications and variations can be made without departing from the spirit and scope of the present invention. Therefore, such modification examples or variation examples should not be individually understood from the technical spirit or perspective of the present invention, and it is to be said that modified exemplary embodiments also belong to the scope of the claims of the present invention.

The invention claimed is:

1. A method for manufacturing an optical fiber emitting plasma light, comprising:
    a coating removal step of removing a coating of an optical fiber;
    a photocatalyst application step of applying a photocatalyst to an end surface of a core layer of the optical fiber from which the coating has been removed through the coating removal step; and
    a molding step of molding the end surface of the core layer into a curved surface by applying a laser to the core layer of the optical fiber applied with the photocatalyst through the photocatalyst application step, wherein the molding step is performed by applying the laser while the optical fiber is erected such that the end surface of the core layer of the optical fiber applied with the photocatalyst through the photocatalyst application step is positioned on an upper surface.

2. The method of claim 1, wherein the core layer of the optical fiber is made of silica.

3. The method of claim 1, wherein the photocatalyst application step is performed by immersing the end surface of the core layer of the optical fiber in the photocatalyst to a depth of 0.4 to 0.6 mm while applying a laser to the core layer of the optical fiber.

4. The method of claim 1, wherein the photocatalyst is made of 100 parts by weight of titanium oxide, 400 to 500 parts by weight of manganese dioxide, 350 to 450 parts by weight of epoxy, and 45 to 55 parts by weight of carbon.

5. The method of claim 1, wherein the laser is applied under a condition of 8 to 10 W, a pulse width of 50 ms, and an off time of 50 ms.

6. The method of claim 1, wherein the laser is irradiated for 1.5 to 2.5 seconds.

7. The method of claim 1, wherein the laser is applied under a condition of 8 to 10 W, a pulse width of 50 ms, and an off time of 50 ms, and the laser is irradiated for 1.5 to 2.5 seconds.

* * * * *